US010285966B2

(12) United States Patent
Yonejima et al.

(10) Patent No.: US 10,285,966 B2
(45) Date of Patent: May 14, 2019

(54) 10-HYDROXY-CIS-12-OCTADECENOIC ACID ALKYL ESTER AND USE THEREOF

(71) Applicants: NITTO PHARMACEUTICAL INDUSTRIES, LTD., Muko-shi, Kyoto (JP); KYOTO UNIVERSITY, Kyoto-shi, Kyoto (JP)

(72) Inventors: Yasunori Yonejima, Muko (JP); Jun Ogawa, Kyoto (JP); Shigenobu Kishino, Kyoto (JP)

(73) Assignees: NITTO PHARMACEUTICAL INDUSTRIES, LTD., Muko (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/578,704

(22) PCT Filed: Jun. 2, 2016

(86) PCT No.: PCT/JP2016/066406
§ 371 (c)(1),
(2) Date: Nov. 30, 2017

(87) PCT Pub. No.: WO2016/195017
PCT Pub. Date: Dec. 8, 2016

(65) Prior Publication Data
US 2018/0318248 A1 Nov. 8, 2018

(30) Foreign Application Priority Data
Jun. 2, 2015 (JP) .................. 2015-112606

(51) Int. Cl.
| | | |
|---|---|---|
| A61K 31/231 | (2006.01) |
| A23D 9/007 | (2006.01) |
| A61K 8/37 | (2006.01) |
| A61Q 1/00 | (2006.01) |
| A61Q 19/00 | (2006.01) |
| C07C 69/732 | (2006.01) |
| A23K 20/158 | (2016.01) |
| A23L 33/12 | (2016.01) |
| A61K 8/36 | (2006.01) |
| A61P 3/04 | (2006.01) |
| A61P 3/06 | (2006.01) |
| A61P 3/10 | (2006.01) |

(52) U.S. Cl.
CPC ............ *A61K 31/231* (2013.01); *A23D 9/007* (2013.01); *A23K 20/158* (2016.05); *A23L 33/12* (2016.08); *A61K 8/361* (2013.01); *A61K 8/37* (2013.01); *A61Q 1/00* (2013.01); *A61Q 19/00* (2013.01); *C07C 69/732* (2013.01); *A61P 3/04* (2018.01); *A61P 3/06* (2018.01); *A61P 3/10* (2018.01)

(58) Field of Classification Search
None
See application file for complete search history.

(56) References Cited

U.S. PATENT DOCUMENTS

| 2006/0217441 A1 | 9/2006 | Akimoto et al. |
| 2015/0125911 A1 | 5/2015 | Ogawa et al. |
| 2015/0259713 A1 | 9/2015 | Piatesi et al. |
| 2015/0342916 A1 | 12/2015 | Ogawa et al. |
| 2016/0000739 A1 | 1/2016 | Ogawa et al. |

FOREIGN PATENT DOCUMENTS

| JP | 2006-521368 A | 9/2006 |
| JP | 2009-051732 A | 3/2009 |
| WO | WO 2013/168310 A1 | 11/2013 |
| WO | WO 2014/037328 A1 | 3/2014 |
| WO | WO 2014/069227 A1 | 5/2014 |
| WO | WO 2014/129384 A1 | 8/2014 |

OTHER PUBLICATIONS

"Chemoinformatics" in Kirk-Othmer Encyclopedia of Chemical Technology, Hugo O. Villar, Published Online: Mar. 12, 2010, Copyright © 2001 by John Wiley & Sons, Inc. pp. 1-24 at p. 17 (Year: 2010).*
Goodman and Gilnnan's The Pharmacological Basis of Therapeutics, McGgraw Hill Medical, 2008, pp. 1-25 (Year: 2008).*
Wallen et al., Lipids (1971), 6(10), 745-50 (Year: 1971).*
Koritala et al., Journal of the American Oil Chemists' Society (1992), 69(6), 575-8 (Year: 1992).*
Faruqi et al., "Synthesis, Spectroscopic Characterization and Evaluation of Anti-Tumor Properties of Novel Fatty Acid Conjugates of 2,4 and 2,6-Diisopropylphenol," *International Journal of Pharmaceutical Sciences and Research*, 6(1): 239-246 (2015).
Koritala et al., "Microbial Conversion of Linoleic and Linolenic Acids to Unsaturated Hydroxy Fatty Acids," *Journal of the American Oil Chemists Society*, 69(6): 575-578 (1992).
Miyamoto et al., "A Gut Microbial Metabolite of Linoleic Acid, 10-Hydroxy-cis-12-octadecenoic Acid, Ameliorates Intestinal Epithelial Barrier Impairment Partially via GPR40-MEK-ERK Pathway," *J. Biol. Chem.*, 290(5): 2902-2918 (2015).
Nagao et al., "Conjugated Fatty Acids in Food and Their Health Benefits," *J. Biosci. Bioeng.*, 100(2): 152-157 (2005).
Japanese Patent Office, International Search Report in International Patent Application No. PCT/JP2016/066406 (dated Aug. 9, 2016).
Black et al., "Antifungal Lipids Produced by Lactobacilli and Their Structural Identification by Normal Phase LC/Atmospheric Pressure Photoionization—MS/MS," *J. Agric. Food Chem.*, 61(22): 5338-5346 (2013).
Takeuchi et al., "Hydroxy fatty acid production by *Pediococcus sp.*," *Eur. J. Lipid Sci. Technol.*, 115(4): 386-393 (2013).

(Continued)

Primary Examiner — Karl J Puttlitz
(74) Attorney, Agent, or Firm — Leydig, Voit & Mayer, Ltd.

(57) ABSTRACT

The invention provides a HYA derivative having superior physiological functions intrinsic to HYA and permitting easy ingestion and easy handling, and use thereof. In particular, the invention relates to an alkyl ester of 10-hydroxy-cis-12-octadecenoic acid, or an optical isomer thereof, or ester of 10-hydroxy-cis-12-octadecenoic acid with dihydric alkanol or an optical isomer thereof, and a composition (edible fat or oil, food, medicament, cosmetic etc.) containing same.

16 Claims, No Drawings

(56) References Cited

OTHER PUBLICATIONS

Takeuchi et al., "Characterization of hydroxy fatty acid dehydrogenase involved in polyunsaturated fatty acid saturation metabolism in *Lactobacillus plantarum* AKU 1009a," *Journal of Molecular Catalysis B: Enzymatic*, 117: 7-12 (2015).
European Patent Office, Extended European Search Report in European Patent Application No. 16803451.0 (dated Jan. 28, 2019).

* cited by examiner

10-HYDROXY-CIS-12-OCTADECENOIC ACID ALKYL ESTER AND USE THEREOF

CROSS-REFERENCE TO RELATED APPLICATIONS

This patent application is the U.S. national phase of International Patent Application No. PCT/JP2016/066406, filed Jun. 2, 2016, which claims the benefit of Japanese Patent Application No. 2015-112606, filed on Jun. 2, 2015, which are incorporated by reference in their entireties herein.

TECHNICAL FIELD

The present invention relates to an alkyl ester of 10-hydroxy-cis-12-octadecenoic acid (hereinafter sometimes to be abbreviated as "HYA"), an ester with dihydric alkanol or an optical isomer thereof.

The present invention also relates to a use of the ester or an optical isomer thereof as edible fat or oil, and a composition (food, medicament, cosmetic, feed etc.) containing the ester or an optical isomer thereof.

BACKGROUND ART

In recent years, the physiological function of scarce fatty acid present only at a low ratio in the body has been attracting attention. For example, it has been reported that conjugated fatty acids such as conjugated linoleic acid and the like (non-patent document 1) and ω3 polyvalent unsaturated fatty acids such as eicosapentaenoic acid, docosahexaenoic acid and the like (patent document 1) have lipid metabolism improving effects, diabetes improving effects and the like. There is a high interest in ingesting the aforementioned scarce fatty acid as functional lipids from the diet, and products (foods, etc.) containing them are on the market.

One of the scarce fatty acids is a hydroxylated fatty acid having a hydroxy group in the compound. The physiological functions thereof have not been analyzed sufficiently heretofore due to the absence of a suitable source of supply. Recently, however, a means for highly efficient and highly selective production by an enzymatic reaction using linoleic acid or the like, which is contained in a large amount in vegetable oil, as a starting material has been found (patent document 2). A method of supplying various hydroxylated fatty acids has been secured, along with which studies on the physiological functions thereof have been actively conducted. The present inventors particularly took note of 10-hydroxy-cis-12-octadecenoic acid (HYA) among hydroxylated fatty acids, and reported that HYA has a lipid metabolic abnormality improving effect (patent document 3), an action to enhance intestinal immunity (patent document 4), a suppressive action on intestinal inflammations (non-patent document 2) and the like.

Since it has become easy to obtain high purity HYA as described above, if HYA can be ingested easily, effective utilization of HYA is expected to be promoted by utilizing its physiological functions. However, since the melting point of HYA is about 25° C. ("about" here means ±1° C.) and HYA is solid (or partially liquefied state) at ambient temperature, there was a problem that it is inferior to liquid components in the ease of ingestion and handleability in adding to or mixing with other liquid or solid food components. In addition, the acrid flavor of HYA is an obstacle in ingestion.

On the other hand, a HYA derivative capable of solving the above-mentioned problems has not been reported heretofore.

As regards alkyl ester of HYA, use of methyl 10-hydroxy-cis-12-octadecenoate and ethyl 10-hydroxy-cis-12-octadecenoate as production intermediates for sebacic acid has been reported (patent document 5); however, they have not been utilized for use other than as the production intermediate. In addition, alkyl ester of HYA other than methyl 10-hydroxy-cis-12-octadecenoate and ethyl 10-hydroxy-cis-12-octadecenoate has not been reported to date.

DOCUMENT LIST

Patent Documents

Patent document 1: National Publication of International Patent Application No. 2006-521368
Patent document 2: WO 2013/168310
Patent document 3: WO 2014/069227
Patent document 4: WO 2014/129384
Patent document 5: WO 2014/037328

Non-Patent Documents

Non-patent document 1: Nagao, K., J. Biosci. Bioeng., 2005, vol. 100, no. 2, p. 152-157
Non-patent document 2: Miyamoto, J., et al., J. Biol. Chem., 2015, 290(5), 2902-2918

SUMMARY OF THE INVENTION

Problems to be Solved by the Invention

The problem of the present invention is to provide a novel HYA derivative having superior physiological functions of HYA and permitting easy ingestion and easy handling.

Means of Solving the Problems

The present inventors have conducted intensive studies in view of the aforementioned problems and clarified that an alkyl ester of 10-hydroxy-cis-12-octadecenoic acid, or an optical isomer thereof, is liquid at ambient temperature and has a good flavor. Further studies have resulted in the completion of the present invention.

That is, the present invention provides the following:
[1] An alkyl ester of 10-hydroxy-cis-12-octadecenoic acid or an optical isomer thereof (excluding methyl 10-hydroxy-cis-12-octadecenoate and ethyl 10-hydroxy-cis-12-octadecenoate).
[2] The alkyl ester of 10-hydroxy-cis-12-octadecenoic acid or an optical isomer thereof of the above-mentioned [1], which is liquid at ambient temperature.
[3] Edible fat or oil comprising an alkyl ester of 10-hydroxy-cis-12-octadecenoic acid or an optical isomer thereof.
[4] A food or food additive comprising an alkyl ester of 10-hydroxy-cis-12-octadecenoic acid or an optical isomer thereof.
[5] A pharmaceutical composition comprising an alkyl ester of 10-hydroxy-cis-12-octadecenoic acid or an optical isomer thereof.
[6] A prophylactic or therapeutic agent for a disease selected from the group consisting of obesity, diabetes, lipid metabolism abnormality, hyperlipidemia, fatty liver, ulcer, ulcerative colitis, Crohn's disease, irritable bowel syndrome and inflammatory diseases, comprising an alkyl ester of 10-hydroxy-cis-12-octadecenoic acid or an optical isomer thereof.

[7] A cosmetic or cosmetics additive comprising an alkyl ester of 10-hydroxy-cis-12-octadecenoic acid or an optical isomer thereof.

[8] A feed or feed additive comprising an alkyl ester of 10-hydroxy-cis-12-octadecenoic acid or an optical isomer thereof.

[9] An ester of 10-hydroxy-cis-12-octadecenoic acid with dihydric alkanol, or an optical isomer thereof.

[10] The ester or an optical isomer thereof of [9], which is liquid at ambient temperature.

[11] A food or food additive comprising the ester or an optical isomer thereof of [9] or [10].

[12] A pharmaceutical composition comprising the ester or an optical isomer thereof of [9] or [10].

[13] A cosmetic or cosmetics additive comprising the ester or an optical isomer thereof of [9] or [10].

Effect of the Invention

According to the present invention, an ester of 10-hydroxy-cis-12-octadecenoic acid with monohydric or dihydric alkanol (an alkyl ester of 10-hydroxy-cis-12-octadecenoic acid and an alkyl ester of 10-hydroxy-cis-12-octadecenoic acid with alkyleneglycol) and an optical isomer thereof (hereinafter these are sometimes to be generically abbreviated as "the compound of the present invention") can be provided. The compound of the present invention is an HYA derivative that is liquid at ambient temperature, has a good flavor, and permits easy ingestion and easy handling.

In addition, in the compound of the present invention, the intramolecular ester bond is hydrolyzed by lipase or the like in the body after ingestion to liberate HYA. Thus, superior physiological functions (lipid metabolic abnormality improving effect, action to increase intestinal immunity, intestinal inflammation suppressive action, etc.) as well as when HYA is ingested singly are expected to be exerted.

Therefore, the compound of the present invention having the above-mentioned functions is industrially extremely useful because it can be utilized as edible fat or oil, and can also be utilized as every kind of food or food additive and further, utilized in various fields such as pharmaceutical product, cosmetic, feed and the like.

DESCRIPTION OF EMBODIMENTS

The present invention is explained in detail below.

Definition

In the present specification, the "acyl (group)" means alkanoyl, alkenoyl or aroyl.

The alkanoyl is formyl, straight chain or branched chain alkylcarbonyl and, for example, formyl, acetyl, propanoyl (propionyl), butanoyl (butyryl), isobutanoyl (isobutyryl), pentanoyl, hexanoyl, heptanoyl and the like can be mentioned.

The alkenoyl is straight chain or branched chain alkenylcarbonyl and, for example, propenoyl (acryl), butenoyl, oleoyl and the like can be mentioned.

The aroyl is arylcarbonyl and, for example, benzoyl, naphthoyl and the like can be mentioned.

In the present specification, the "alkyl (group)" means a straight chain or branched chain alkyl group having a carbon atom number of one or more. When a particular limitation on the carbon number is absent, it is generally a $C_{1-40}$ alkyl group, preferably a $C_{1-20}$ alkyl group, particularly preferably a $C_{1-6}$ alkyl group, most preferably a $C_{1-3}$ alkyl group.

In the present specification, the "$C_{1-40}$ alkyl (group)" means a straight chain or branched chain alkyl group having a carbon number of 1-40. For example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, tetradecyl, hexadecyl, octadecyl, eicosyl, tetracosyl, octacosyl, triacontyl, dotriacontyl, hexatriacontyl, tetracontyl and the like can be mentioned.

In the present specification, the "$C_{1-20}$ alkyl (group)" means a straight chain or branched chain alkyl group having a carbon number of 1-20. For example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, tetradecyl, hexadecyl, octadecyl, eicosyl and the like can be mentioned.

In the present specification, the "$C_{1-6}$ alkyl (group)" means a straight chain or branched chain alkyl group having a carbon number of 1-6. For example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like can be mentioned.

In the present specification, the "$C_{1-3}$ alkyl (group)" means a straight chain or branched chain alkyl group having a carbon number of 1-3. For example, methyl, ethyl, propyl, isopropyl and the like can be mentioned.

In the present specification, the "alkyl ester" of the "alkyl ester of 10-hydroxy-cis-12-octadecenoic acid" or "alkyl ester of fatty acid" means an ester formed from alcohol having an alkyl group defined above (monohydric alkanol) and 10-hydroxy-cis-12-octadecenoic acid or fatty acid. The alkyl group constituting the "alkyl ester" is optionally substituted.

In the present specification, the "monoester of 10-hydroxy-cis-12-octadecenoic acid with alkyleneglycol" and "diester of 10-hydroxy-cis-12-octadecenoic acid ester with alkyleneglycol" respectively mean monoester and diester of dihydric alkanol (alkanediol) and 10-hydroxy-cis-12-octadecenoic acid. The alkyleneglycol constituting the monoester or diester is optionally substituted.

The "alkyleneglycol" in the above means dihydric straight chain or branched chain alkanol (alkanediol). The alkyleneglycol in the present invention is generally $C_{1-8}$ alkyleneglycol, preferably $C_{2-6}$ alkyleneglycol, more preferably $C_{2-4}$ alkyleneglycol. The two hydroxy groups in the alkyleneglycol may be bonded to any position of the alkylene chain as long as it can form an ester with 10-hydroxy-cis-12-octadecenoic acid.

As used herein, the "$C_{1-8}$ alkyleneglycol" refers to a dihydric alkanol having a carbon number of 1-8, the "$C_{2-6}$ alkyleneglycol refers to a dihydric alkanol having a carbon number of 2-6, and the "$C_{2-4}$ alkyleneglycol" refers to a dihydric alkanol having a carbon number of 2-4.

Specific examples of the alkyleneglycol include methyleneglycol (methanediol), ethylene glycol (ethanediol), 1,2-propylene glycol (1,2-propanediol), 1,3-propylene glycol (1,3-propanediol), 1,3-butyleneglycol (1,3-butanediol), 1,2-pentyleneglycol (1,2-pentanediol), 1,2-hexyleneglycol (1,2-hexanediol), hexyleneglycol (2-methyl-2,4-pentanediol), 1,2-octyleneglycol (1,2-octanediol) and the like. Ethylene glycol (ethanediol), 1,2-propylene glycol (1,2-propanediol), 1,3-propylene glycol (1,3-propanediol), 1,3-butyleneglycol (1,3-butanediol), 1,2-pentyleneglycol (1,2-pentanediol), 1,2-hexyleneglycol (1,2-hexanediol), hexyleneglycol (2-methyl-2,4-pentanediol) and the like are preferable, and ethylene glycol (ethanediol), 1,2-propylene glycol (1,2-propanediol), 1,3-propylene glycol (1,3-propanediol), 1,3-butyleneglycol (1,3-butanediol) and the like are more preferable.

In the present specification, the "alkylene (group)" is a divalent substituent of straight chain or branched chain alkane having a carbon number of one or more, generally a $C_{1-8}$ alkylene group, preferably a $C_{2-6}$ alkylene group, and more preferably a $C_{2-4}$ alkylene group.

In the present specification, the "$C_{1-8}$ alkylene (group)" means a straight chain or branched chain alkylene group having a carbon number of 1-8. For example, methylene, ethylene, propylene, 1-methylethylene, butylene, 1-methylpropylene, pentylene, 1-propylethylene, hexylene, 1-butylethylene, 1,1,3-trimethylpropylene, heptylene, octylene, 1-hexylethylene and the like can be mentioned.

In the present specification, the "$C_{2-6}$ alkylene (group)" means a straight chain or branched chain alkylene group having a carbon number of 2-6. For example, ethylene, propylene, 1-methylethylene, butylene, 1-methylpropylene, pentylene, 1-propylethylene, hexylene, 1-butylethylene, 1,1,3-trimethylpropylene and the like can be mentioned.

In the present specification, the "$C_{2-4}$ alkylene(group)" means a straight chain or branched chain alkylene group having a carbon number of 2-4. For example, ethylene, propylene, 1-methylethylene, butylene, 1-methylpropylene and the like can be mentioned.

In the present specification, being "optionally substituted" means optionally having one or more substituents. The "substituent" is not particularly limited, and includes, for example, a halogen atom, an optionally protected hydroxy group (e.g., hydroxy group, $C_{1-6}$ alkoxy group, $C_{1-7}$ alkanoyloxy group, $C_{7-11}$ aroyloxy group, $C_{1-6}$ alkylsulfonyloxy group, $C_{6-10}$ arylsulfonyloxy group, hydroperoxy group etc.), an optionally protected mercapto group (e.g., mercapto group, methylthio group, acetylthio group etc.), an optionally protected carboxy group (e.g., a carboxy group, $C_{1-6}$ alkoxy-carbonyl group etc.), an optionally protected amino group (e.g., amino group, methylamino group, acetylamino group, dimethylamino group etc.), an acyl group (e.g., $C_{1-7}$ alkanoyl group, $C_{7-11}$ aroyl group etc.), a carbamoyl group optionally substituted by a $C_{1-6}$ alkyl group, a nitro group, a cyano group, a $C_{3-8}$ cycloalkyl group, an oxiranyl group, a $C_{6-10}$ aryl group and the like. When plural substituents are present, the respective substituents may be the same or different.

In the present specification, the "optionally protected hydroxy group", "optionally protected mercapto group", "optionally protected carboxy group" or "optionally protected amino group" means a hydroxy group, a mercapto group, a carboxy group, or an amino group optionally protected by a "protecting group". As the "protecting group", protecting groups of a hydroxy group, a mercapto group, a carboxy group, or an amino group described in Protective Groups in Organic Synthesis, John Wiley and Sons (1980) can be used. For example, protecting groups such as $C_{1-6}$ alkyl group, $C_{7-14}$ aralkyl group, $C_{6-10}$ aryl group, $C_{1-7}$ alkanoyl group, $C_{7-14}$ aralkyl-carbonyl group, tri $C_{1-6}$ alkylsilyl group and the like can be mentioned. The above-mentioned protecting group is optionally further substituted by a halogen atom, a $C_{1-6}$ alkyl group, a $C_{1-6}$ alkoxy group or a nitro group. In addition, the "optionally protected hydroxy group", "optionally protected mercapto group", "optionally protected carboxy group" and "optionally protected amino group" also encompass a hydroxy group, a mercapto group, a carboxy group or an amino group, to which a group derived from a natural product such as sugar, amino acid, fatty acid, nucleic acid, phosphoric acid, sulfuric acid and the like is bonded.

(The Compound of the Present Invention)

In one embodiment of the present invention, the compound of the present invention is an alkyl ester of 10-hydroxy-cis-12-octadecenoic acid or an optical isomer thereof (hereinafter sometimes to be referred to as "compound (1) of the present invention" in the present specification).

In another embodiment of the present invention, the compound of the present invention is a monoester formed from 10-hydroxy-cis-12-octadecenoic acid and dihydric alkanol (to be also referred to as "monoester of 10-hydroxy-cis-12-octadecenoic acid with alkyleneglycol") or an optical isomer thereof (hereinafter sometimes to be referred to as "compound (2) of the present invention" in the present specification).

In still another embodiment of the present invention, the compound of the present invention is a diester formed from 10-hydroxy-cis-12-octadecenoic acid and dihydric alkanol (to be also referred to as "diester of 10-hydroxy-cis-12-octadecenoic acid with alkyleneglycol") or an optical isomer thereof (hereinafter sometimes to be referred to as "compound (3) of the present invention" in the present specification).

The compound (1) of the present invention is specifically an alkyl ester of 10-hydroxy-cis-12-octadecenoic acid represented by the following formula (I):

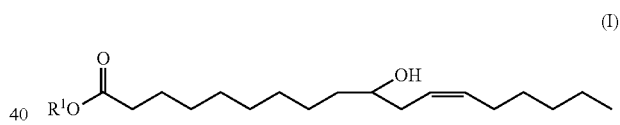

(I)

wherein $R^1$ is an optionally substituted alkyl group, or an optical isomer thereof.

In the formula (I), the optionally substituted alkyl group for $R^1$ is as defined above.

The compound (1) of the present invention may be an ester formed from one kind of monohydric alkanol and 10-hydroxy-cis-12-octadecenoic acid, or a mixture of esters formed from two or more kinds of monohydric alkanol and 10-hydroxy-cis-12-octadecenoic acid.

The compound (2) of the present invention is specifically a monoester of 10-hydroxy-cis-12-octadecenoic acid with alkyleneglycol represented by the following formula (II):

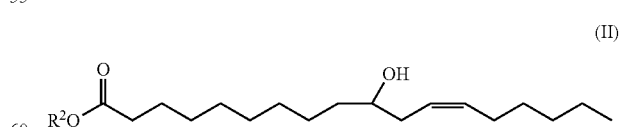

(II)

wherein $R^2$ is a residue of optionally substituted alkyleneglycol,
or an optical isomer thereof.

In the formula (II), the residue of optionally substituted alkyleneglycol for $R^2$ is the residue of alkyleneglycol defined above.

The compound (2) of the present invention may be a monoester formed from one kind of dihydric alkanol (alkyleneglycol) and 10-hydroxy-cis-12-octadecenoic acid, or a mixture of monoester formed from two or more kinds of dihydric alkanol (alkyleneglycol) and 10-hydroxy-cis-12-octadecenoic acid.

The compound (3) of the present invention is specifically a diester of 10-hydroxy-cis-12-octadecenoic acid with alkyleneglycol represented by the following formula (III):

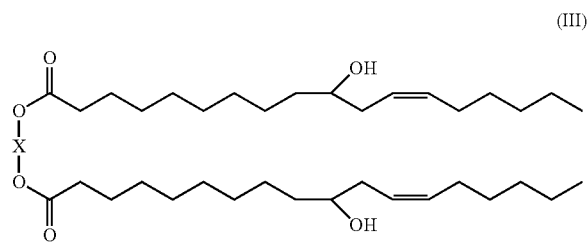

(III)

wherein X is an optionally substituted alkylene group, or an optical isomer thereof.

In the formula (III), the optionally substituted alkylene group for X is as defined above.

The compound (3) of the present invention may be a diester formed from one kind of dihydric alkanol (alkyleneglycol) and 10-hydroxy-cis-12-octadecenoic acid, or a mixture of diester formed from two or more kinds of dihydric alkanol (alkyleneglycol) and 10-hydroxy-cis-12-octadecenoic acid.

When compounds (1)-(3) of the present invention has an isomer such as optical isomer, stereoisomer, regio isomer and the like, any isomer and a mixture thereof are each encompassed in compounds (1)-(3) of the present invention. They can be each obtained as an optically pure compound by a known synthesis method, separation method (recrystallization method, separation by high performance liquid chromatography using optically active column, enzyme method etc.) and the like. The optical isomers may be used in a mixed state, or optically pure compounds each obtained by separation may be used singly, or they may be used in combination.

The compounds (1)-(3) of the present invention are desirably liquid at ambient temperature. In the present specification, the ambient temperature refers to the ambient temperature (15° C.-25° C.) defined in the Japanese Pharmacopoeia, 16th edition, General Rules, the Japanese Pharmacopoeia, 17th edition, General Rules. In addition, "about" here means ±1° C.

Of the compounds of the present invention, compounds (2) and (3) of the present invention can also be utilized as a food or food additive. They are particularly suitable for use as, among the below-mentioned pharmaceutical compositions, a composition to be parenterally administered, and use as cosmetics or cosmetics additive.

(Production Method of the Compound of the Present Invention)

The production method of the compound of the present invention is not particularly limited. For example, a production method including esterification by reacting HYA or an activated form thereof (e.g., acid halide, active ester, acid anhydride etc.) with alkanol (monohydric or dihydric alkanol) (production method 1), and a production method including transesterification of HYA or an activated form thereof (e.g., acid halide, active ester, acid anhydride etc.) and alkyl ester or alkyleneglycol ester of fatty acid (hereinafter to be abbreviated as fatty acid ester) (production method 2) can be mentioned. As the production method and reaction conditions, preferable ones can be selected in consideration of the stability of the starting compound and resultant product and the like, and plural production methods can also be combined. Furthermore, reaction steps such as protection, deprotection and the like can also be combined as appropriate.

HYA used in each of the above-mentioned production methods can be prepared by the method described in patent document 2 and the like. The alkanol, and fatty acid or an activated form thereof (e.g., acid halide, active ester, acid anhydride etc.) to be used for the above-mentioned respective production methods may be commercially available products, or can be synthesized from commercially available starting compounds according to a method known per se, or a method analogous thereto, and utilized.

The production method 1 of compound of the present invention is explained below.

The esterification step of production method 1 can be performed using an enzymatic reaction or a chemical reaction. An enzymatic reaction is preferably used since the reaction operation is convenient and the reaction conditions are mild.

The enzyme to be used for the esterification reaction of production method 1 is not particularly limited as long as it can cause conversion to the compound of the present invention. For example, lipase, esterase and the like can be mentioned, and lipase is preferable. Lipase can be purchased as a commercially available product from Novozymes A/S, Amano Enzyme Inc., Meito Sangyo Co., Ltd., Sigma-Aldrich Co. LLC and the like.

As alkanol to be used as the reaction substrate in production method 1, any monohydric or dihydric alkanol can be used without particular limitation as long as it affords the compound of the present invention by an esterification reaction with HYA.

As monohydric alkanol, alkanol having a carbon number of 1-40 can be mentioned, and methanol, ethanol, propanol and the like are preferable.

As dihydric alkanol, alkanediol having a carbon number of 1-8 can be mentioned. Alkanediol having a carbon number of 2-6 is preferable, and alkanediol having a carbon number of 2-4, for example, ethylene glycol, propylene glycol and butyleneglycol are more preferable.

In the esterification step of production method 1, the water content of the reactant and solvent is desirably as small as possible so that compounds (1)-(3) of the present invention as the reaction products will not be hydrolyzed. The reaction can be performed without solvent or in various non-aqueous solvents (e.g., non-polar solvents such as n-heptane, n-hexane, isooctane and the like), and reaction without solvent is more preferable. Furthermore, the esterification reaction may be accelerated by removing water from the reaction system to shift the reaction equilibrium or the reaction can also be carried out under reduced pressure to reduce the water content of the reactant and solvent to be used.

The reaction temperature of production method 1 varies depending on the presence or absence of the solvent, the kind of solvent when a solvent is used, the kind of enzyme, the state of HYA as the reaction substrate (kind of activated form etc.), the kind of alkanol and the like. It is generally 4° C.-100° C., preferably 20° C.-70° C., more preferably 30° C.-50° C.

The reaction time of production method 1 varies depending on the presence or absence of the solvent, the kind of solvent when a solvent is used, the kind of enzyme, the state of HYA as the reaction substrate (kind of activated form etc.), the kind of alkanol and the like. It is generally 1 hr-168 hr, preferably 5 hr-48 hr.

While the amounts of HYA and alkanol to be used as reaction substrates in production method 1 also depend on the kind of alkanol, 10 wt %-1000 wt % is preferable, 30 wt %-500 wt % is more preferably, 50 wt %-300 wt % is particularly preferable, relative to HYA.

The amount of enzyme to be used as a reactant in production method 1 relative to that of HYA is preferably 1 wt %-100 wt %, more preferably 1 wt %-50 wt %, particularly preferably 1 wt %-20 wt %.

The enzyme to be used for the enzymatic reaction used in the above-mentioned production method 1 may be immobilized by various carriers or may be of a free type. The immobilized ones are more preferable since they are highly active even in an anhydrous reaction system and also in a reaction system with a small amount of water, and can be recovered and used repeatedly. The above-mentioned enzymes may be purified or crude products. The enzymes may be expressed in bacteria such as *Escherichia coli* or the like and the bacterial cells themselves may be used or culture broth of the bacterial cells may be used.

(Edible Fats and Oils in the Present Invention)

The present invention provides edible fats and oils containing compound of the present invention (hereinafter to be also referred to as "edible fats and oils the present invention" in the present specification).

That is, compound of the present invention can singly provide edible fats and oils, or blended with other edible fats and oils to give edible fats and oils. While the content of compound of the present invention in the edible fats and oils of the present invention is not particularly limited, it is generally not less than 5 wt %, preferably not less than 20 wt %, more preferably not less than 50 wt %, relative to the total amount of edible fats and oils. It is particularly preferable to use edible fats and oils singly because superior flavor and physiological function can be obtained.

The edible fats and oils of the present invention may contain, for example, general components (food additive etc.), which are used for edible fats and oils, as long as the characteristics of the present invention are not impaired. Examples of these components include emulsifier, oxidation/degradation inhibitor, antifoaming agent, crystal adjuster and the like.

Examples of the emulsifier include glycerol fatty acid ester, polyglycerol fatty acid ester, sucrose fatty acid ester, polyglycerol condensed ricinoleic acid ester, sorbitan fatty acid ester, propylene glycol ester of fatty acid, polyoxyethylene sorbitan fatty acid ester, organic acid monoglyceride and the like.

Examples of the oxidation/degradation inhibitor include tocopherols, flavone derivative, gallic acid derivative, catechin and ester thereof, lignans (e.g., sesamine and the like), fukiic acid, sesamol, terpenes and the like.

Examples of the antifoaming agent include silicone oil and the like.

Examples of the crystal adjuster include triacylglycerol, diacylglycerol, monofatty acid glyceryl, heptafatty acid decaglyceryl, decafatty acid decaglyceryl, waxes, sterol esters and the like.

In addition, spice, colorant and the like can also be added. Examples of the spice include capsaicin, anethole, eugenol, cineol, zingerone and the like. Examples of the colorant include carotene, astaxanthin and the like.

Furthermore, the edible fats and oils of the present invention may also contain various nutrients (carbohydrates, protein etc.), various vitamins (vitamin A, vitamin $B_1$, vitamin $B_2$, vitamin $B_6$, vitamin C, vitamin D, vitamin E, vitamin K etc.), various minerals (magnesium, zinc, iron, sodium, potassium, selenium etc.) and the like as necessary.

(Food or Food Additive of the Present Invention)

The present invention provides a food or food additive containing compound of the present invention (hereinafter to be also referred to as "food or food additive of the present invention" in the present specification).

The food or food additive of the present invention is not particularly limited as long as it is in an orally ingestible form such as solution, suspension, emulsion, gel, powder, solid molded product and the like.

Specific examples of the food or food additive of the present invention include supplement (powder, granule, soft capsule, hard capsule, tablet, chewable tablet, quick-integrating tablet, syrup, liquid etc.), drinks (carbonated drinks, lactic drinks, sports drinks, fruit juice drinks, vegetable drinks, soymilk drink, coffee drinks, tea drinks, powder drinks, concentration drinks, nutritional beverage, alcoholic drinks etc.), confectionery (gummi candy, jelly, gum, chocolate, cookie, candy, caramel candy, Japanese confectionery, snack food etc.), table-ready foods (instant noodles, retort food, canned food, microwave food, instant soup, miso soup, freeze-dry food etc.), fats and oils food (mayonnaise, dressing, butter, cream, margarine etc.), wheat flour product (bread, pasta, noodle, cake mixture, breadcrumbs etc.), seasoning (sauce, tomato processing seasoning, flavor seasoning, mixture for cooking, seasoning soy sauce etc.), and processed meat product (meat ham, sausage etc.) and the like.

The content of compound of the present invention in the food or food additive of the present invention is 5 wt %-90 wt %, preferably 10 wt %-80 wt %, more preferably 20 wt %-70 wt %, relative to the total amount of the food or food additive.

The daily ingestion amount of the food or food additive of the present invention is appropriately determined according to the age of the subject who ingests the food or food additive, symptoms and conditions and the severity thereof expected to be improved by the ingestion, dosage form of food and the like, and the like. It is preferable that the ingestion amount of compound of the present invention is set to such amount as will be similar to the below-mentioned daily dose.

The food or food additive of the present invention can be blended with various nutrients (carbohydrates, protein etc.), various vitamins (vitamin A, vitamin $B_1$, vitamin $B_2$, vitamin $B_6$, vitamin C, vitamin D, vitamin E, vitamin K etc.), various minerals (magnesium, zinc, iron, sodium, potassium, selenium etc.), dietary fiber, food with reported physiological function (royal jelly, propolis, agaricus etc.) and the like as necessary.

In addition, the food or food composition of the present invention can contain, as necessary, general food additives, for example, emulsifier (glycerol fatty acid ester, sucrose fatty acid ester etc.), thickening stabilizer (pectin, sodium carboxymethylcellulose etc.), antioxidant (mixed vitamin E, sodium erythorbate etc.), preservative (sodium benzoate, sorbic acid etc.), gloss agent (shellac, beeswax etc.), sweetener (xylitol, aspartame etc.), acidulant (citric acid, malic acid etc.), bittering agent (caffeine, naringin etc.), seasoning (sodium L-glutamate, disodium 5'-inosinate etc.), colorant (gardenia yellow dye, red No. 2 etc.), flavor (orange flavor, vanillin etc.), manufacturing agent (brine, binding agent etc.) and the like.

The food or food additive of the present invention can be prepared by a general production method by adding the above-mentioned various nutrients, various vitamins and the like, and general food additives as necessary to compound of the present invention.

The above-mentioned edible fats and oils, and food or food additive of the present invention also encompasses those classified in the health food, functional food, food with health claims (e.g., food for specified health uses, foods with function claims etc.), food for special dietary uses (e.g., food for patient etc.), edible fats and oils and foods with a disease risk reduction indication and the like.

Examples of the "disease risk reduction indication" is, for example, an indication that it is for treating, improving, suppressing and/or preventing diseases whose symptoms can be improved by HYA. Therefore, the edible fats and oils, food or food additive of the present invention can be provided as edible fats and oils, food or food additive with an indication that it is for the improvement and/or prophylaxis of the diseases whose symptoms can be improved by HYA; for example, obesity, diabetes, lipid metabolic abnormality, hyperlipidemia, fatty liver, inflammatory bowel disease (ulcerative colitis, Crohn's disease, pseudomembranous enteritis etc.), ulcer, irritable bowel syndrome, and various other inflammatory diseases (e.g., gout, arthritis, polyneuritis, polyneuroradiculitis, hepatitis, bronchitis, pneumonia, nephritis, cystitis, periodontal disease, dermatitis, atopic dermatitis etc.).

(The Pharmaceutical Composition of the Present Invention)

The present invention provides a pharmaceutical composition containing compound (I) of the present invention (hereinafter to be also referred to as "the pharmaceutical composition of the present invention" in the present specification).

The pharmaceutical composition of the present invention can be used as a prophylactic agent for preventing, or a therapeutic agent for treating, improving or suppressing diseases whose symptoms can be improved by HYA, in animals, for example, obesity, diabetes, lipid metabolic abnormality, hyperlipidemia, fatty liver, inflammatory bowel disease (ulcerative colitis, Crohn's disease, pseudomembranous enteritis etc.), ulcer, irritable bowel syndrome, and various other inflammatory diseases (e.g., gout, arthritis, polyneuritis, polyneuroradiculitis, hepatitis, bronchitis, pneumonia, nephritis, cystitis, periodontal disease, dermatitis, atopic dermatitis etc.).

As used herein, the "animal" includes mammals such as human, dog, cat, rabbit, hamster, rat, mouse, bovine, swine, sheep, horse, donkey, camel and the like.

The pharmaceutical composition of the present invention is not particularly limited, and can be provided, for example, as an oral preparations in various dosage forms such as powder, granule, pill, soft capsule, hard capsule, tablet, chewable tablet, quick-integrating tablet, syrup, liquid, suspension, emulsion and the like; and a parenteral preparation such as suppository, ointment, cream, gel, adhesive preparation, inhalant, injection and the like.

The pharmaceutical composition of the present invention can be produced by adding various additives as necessary to compound of the present invention and according to a general formulation means, for example, the methods described in the Japanese Pharmacopoeia 16th edition Preparation General Rules [2] Monographs for Preparations, the Japanese Pharmacopoeia 17th edition Preparation General Rules [3] Monographs for Preparations and the like, and the like.

In the present invention, the additives that can be used for formulation are not particularly limited. For example, animal and plant fats and oils such as soybean oil, safflower oil, olive oil, germ oil, sunflower oil, beef tallow, sardine oil and the like; polyhydric alcohols such as polyethylene glycol, propylene glycol, glycerol, sorbitol and the like; surfactants such as sorbitan fatty acid ester, sucrose fatty acid ester, glycerol fatty acid ester, polyglycerol fatty acid ester and the like; solvents such as purified water, sterile purified water, water for injection, physiological saline, ethanol, isopropanol and the like; excipients such as lactose, starch, crystalline cellulose, D-mannitol, soybean lecithin, gum arabic, sorbitol solution, starch syrup and the like; binders such as pregelatinized starch, carboxymethylcellulose, hydroxypropylcellulose, shellac and the like; disintegrants such as crospovidone, povidone, dextrin and the like; lubricants such as magnesium silicate, aluminum stearate, talc and the like; sweetening agents such as aspartame, licorice extract, saccharin sodium and the like; colorants such as yellow iron oxide, brown iron oxide, black iron oxide, Food blue No. 1, Food Red No. 2 and the like; pH adjusters such as hydrochloric acid, citric acid, sodium citrate, potassium hydroxide, sodium hydroxide and the like; flavors such as bitter essence and the like and the like can be mentioned.

When a liquid preparation is produced, a solid preparation to be used by dissolving or suspending in water or other appropriate solvent when in use may be produced. Tablets and granules may be coated by a well-known method.

In the pharmaceutical composition of the present invention, as long as the effect of the present invention is not impaired, a therapeutic drug for the above-mentioned diseases that can be improved or prevented by the pharmaceutical composition of the present invention may be used in combination with compound of the present invention.

Examples of the drug that can be used in combination with the pharmaceutical composition of the present invention (hereinafter to be also referred to as "concomitant drug" in the present specification) include therapeutic drugs for diabetes such as sulfonylurea (tolbutamide, glyclopyramide, glybuzole, glimepiride etc.), biguanide (metformin hydrochloride etc.), α-glucosidase inhibitor (voglibose, acarbose etc.), thiazolidine derivative (pioglitazone hydrochloride etc.) and the like; therapeutic drugs for hyperlipidemia such as statins (pravastatin sodium, simvastatin, pitavastatin calcium etc.), anion exchange resin (colestyramine, colestimide etc.), fibrates (clofibrate, clinofibrate etc.), nicotinic acids (nicotinic acid tocopherol, nicomol etc.) and the like; therapeutic drugs for inflammatory bowel diseases (Crohn's disease, ulcerative colitis, pseudomembranous enteritis etc.) such as salicylic acid preparation (mesalazine etc.), sustainable sulfonamide (salazosulfapyridine etc.), adrenal cortical steroid (betamethasone, predonisolone etc.), molecular-targeted therapeutic drug (infliximab, adalimumab etc.), immunosuppressant (azathioprine etc.) and the like; therapeutic drugs for irritable bowel syndrome such as anticholinergic drug (pipethanate hydrochloride, mepenzolate bromide etc.), gastrointestinal motility regulating agents (trimebutine etc.), synthesized polymer compound (polycarbophil calcium etc.), lactobacillus preparation and the like; therapeutic drugs for gout such as prophylactic drug for gout attack (colchicine etc.), uricosuric drug (probenecid, bucolome, benzbromarone etc.), uric acid synthesis inhibitor (allopurinol etc.) and the like; therapeutic drugs for arthritis, neuritis such as non-steroidal antiinflammatory agents (mefenamic acid, ketoprofen, diclofenac sodium etc.), biological active drug (cyclosporine etc.) and the like; therapeutic drugs for hepatitis such as interferon preparation (interferon β, interferon α-2a etc.), anti-hepatitis virus drug (ribavirin, lamivudine etc.), liver function improvement drug (glycyrrhizin preparation, glucuronic acid, tiopronin etc.) and the like; therapeutic drugs for bronchitis such as n-agonist (ephedrine hydrochloride, dl-methylephedrine hydrochloride, trimetoquinol hydrochloride etc.), theophyllines (diprophylline, aminophylline etc.), anticholinergic drug (thiotropium bromide hydrate etc.) and the like; therapeutic drugs for pneumonia such as macrolide antibiotics (clarithromycin, azithromycin etc.), newquinolone antibiotics (levofloxacin, garenoxacin etc.) and the like; therapeutic drugs for nephritis such as angiotensin converting enzyme inhibitor (enalapril maleate, delapril hydrochloride etc.), angiotensin II receptor antagonists (losartan potassium, candesartan cilexetil etc.) and the like; therapeutic drugs for cystitis such as newquinolone antibiotics (ofloxacin, levofloxacin, norfloxacin etc.), penicillin antibiotics (amoxicillin, ampicillin, cloxacillin etc.), cephem antibiotics (cefcapene pivoxil hydrochloride, cefotiam hexetil hydrochloride etc.), chinese medicine (hatimi-ziôgan, Umbellate Fungus Decoction etc.) and the like; therapeutic drugs for periodontal disease such as cephem antibiotics (cephalexin etc.), antimicrobial agent (benzethonium chloride, chlorhexidine hydrochloride etc.) and the like; therapeutic agents for dermatitis, atopic dermatitis such as non-steroidal antiinflammatory agents (bufexamac, ufenamate etc.), antipruritic drug (Crotamiton etc.) and the like; therapeutic agents for atopic dermatitis such as immunomodulative drug (tacrolimus hydrate etc.) and the like, and the like.

When the pharmaceutical composition of the present invention is produced as a parenteral preparation such as injection and the like, while the composition is not particularly limited, for example, it is preferably administered intravenously, intraperitoneally, intramuscularly, subcutaneously, transdermally, intra-articularly, intrasynovially, intramedullary, sublingually, intraorally and the like, particularly preferably intravenously or intraperitoneally. The intravenous administration may be any of drip administration and bolus administration.

The content of compound of the present invention in the pharmaceutical composition of the present invention is 5 wt %-100 wt %, preferably 10 wt %-90 wt %, more preferably 20 wt %-80 wt %, relative to the total amount of the pharmaceutical composition of the present invention.

The dose of the pharmaceutical composition of the present invention can be appropriately determined according to the kind, age and body weight, symptom and severity of the animal to be the subject of administration, the dosage form and administration method of the pharmaceutical composition, the kind of the concomitant drug and the like. For example, when the pharmaceutical composition of the present invention is orally administered to human, it can be administered at 0.02 mg/kg body weight-100 mg/kg body weight, preferably 0.2 mg/kg body weight-50 mg/kg body weight, as the total amount converted to HYA as the active ingredient, to an adult daily. In addition, when the pharmaceutical composition is parenterally administered to human, it can be administered at 0.002 mg/kg body weight-50 mg/kg body weight, preferably 0.02 mg/kg body weight-50 mg/kg body. The aforementioned dose can be administered once a day or in several portions (2-5 times) for both the oral administration and parenteral administration.

In addition, the dosing period of the pharmaceutical composition of the present invention can be appropriately determined according to the condition, symptom and severity and the like of the animal that receives administration, and is generally 1 day-90 days, preferably 7 days-30 days.

(The Cosmetics or Cosmetics Additive of the Present Invention)

The present invention provides cosmetics or cosmetics additive containing compound of the present invention (hereinafter to be referred to as "cosmetics or cosmetics additive of the present invention" in the present specification).

The cosmetics of the present invention can be prepared by adding various additives as necessary to compound of the present invention, and according to the production method of the above-mentioned pharmaceutical composition.

The cosmetics of the present invention can be produced as cosmetics having various shapes such as skin cosmetics such as cream, gel, milky lotion, serum, toner, microemulsion essence, facial mask and the like; makeup cosmetics such as foundation, lip rouge, eye shadow, cheek color and the like; cleaning cosmetics such as cleansing oil, cleansing cream and the like; hair cosmetics such as shampoo, conditioner and the like; bathing powder and the like.

The cosmetics of the present invention may contain additives, which are generally used for cosmetics, as long as the characteristics of the present invention are not impaired. Examples thereof include active ingredients of antiwrinkle•anti-aging agent, anti-inflammatory agent, skin damage inhibitor, cell activator and wound healing agent, whitening agent and the like, oil (animal and plant fats and oils, wax, ester, higher fatty acid, higher aliphatic alcohol etc.), surfactant, solvent, thickener, humectant, antioxidant, preservative, pH adjuster, pigment, flavor and the like.

The cosmetic additive of the present invention can be produced as a form such as oil, suspension, milk, paste, powder, granule and the like by adding, as necessary, the above-mentioned oil, surfactant, solvent, thickener, pigment and the like to compound of the present invention, and according to the above-mentioned production method of the pharmaceutical composition.

The content of compound of the present invention in the cosmetics or cosmetics additive of the present invention is 5 wt %-70 wt %, preferably 10 wt %-60 wt %, more preferably 20 wt %-50 wt %, relative to the total amount of the cosmetics and the like of the present invention.

(The Feed or Feed Additive of the Present Invention)

The present invention provides a feed or feed additive containing compound (I) of the present invention (hereinafter to be also referred to as "feed or feed additive of the present invention" in the present specification).

The feed or feed additive of the present invention can be produced as a form such as oil, suspension, emulsion, gel, powder, granule, tablet and the like.

As the feed or feed additive of the present invention, pet food, farming or aquaculture feed additive and the like can be mentioned.

The feed or feed additive of the present invention can be prepared according to a general method by mixing compound of the present invention with filler substances, dilution substances and the like for feed.

The filler substances, dilution substances and the like for feed can be used without particular limitation as long as the characteristics of the present invention are not impaired. For example, polysaccharides such as gum arabic, carrageenan, agar, xanthan gum, chitosan, cellulose, locust bean gum and the like; monosaccharides or disaccharides such as glucose, lactose, maltose, sucrose and the like; sugar alcohols such as glycerol, sorbitol, D-mannitol and the like; proteins such as albumin, casein, gluten, gelatin and the like; grain powders such as toasted soybean flour, wheat flour, soy flour, corn flour and the like; yeasts such as torula yeast, bread yeast, beer yeast and the like; fats and oils such as hydrogenated oil, vegetable fat and oil, animal-derived fats and oils and the like; clay minerals such as kaolin, zeolite, talc, vermiculite, bentonite and the like; silicic acids such as diatomaceous earth, hydrated silicon dioxide, silicic acid, light anhydrous silicic acid, silicic anhydride, calcium silicate, magnesium silicate and the like or a salt thereof; hydrocarbons such as light liquid paraffin, liquid paraffin and the like; wax such as carnauba wax and the like, and the like can be mentioned.

Furthermore, the feed or feed additive of the present invention can contain, as long as the characteristics of the present invention are not impaired, additives for nutrition component supplementation, amino acids such as glycine, DL-alanine, sodium L-glutamate and the like or a salt thereof; vitamins such as L-ascorbic acid, ergocalciferol, thiamine hydrochloride, cholecalciferol, vitamin A powder, vitamin D powder, riboflavin and the like; minerals such as potassium chloride, ferric citrate, calcium gluconate and the like; and dyes such as astaxanthin, canthaxanthin and the like.

The content of compound of the present invention in the feed or feed additive of the present invention is 1 wt %-70 wt %, preferably 3 wt %-50 wt %, more preferably 5 wt %-30 wt %, relative to the total amount of the feed and the like of the present invention.

EXAMPLES

The present invention is explained in detail in the following by referring to Examples and Experimental Examples, which are not to be construed as limitative. The invention may be changed within the scope of the present invention.

In the following Examples, proton nuclear magnetic resonance ($^1$H NMR) spectrum was measured using AVANCE III 500 manufactured by Bruker and deuterochloroform as a solvent. The data of $^1$H NMR are reported as chemical shift (δ ppm), multiplicity (s=singlet, d=doublet, t=triplet, q=quartet, m=multiplet, dd=double doublet, dt=double triplet, tt=triple triplet, brs=broad singlet, sep=septet), coupling constant (Hz), integration and allocation.

High resolution mass spectrometry was performed using high-speed liquid chromatograph mass spectrometer (LCMS) (LCMS-2020) manufactured by Shimadzu Corporation.

Melting point (mp) was measured using melting point measuring instrument (MP-J3) manufactured by Anatec Yanaco Inc.

In the following Examples, the compounds (1)-(3) of the present invention were produced according to the above-mentioned production method 1. The alkanol (ethanol, propanol and ethylene glycol) used for the production of the compounds of the present invention is a commercially available product (manufactured by Wako Pure Chemical Industries, Ltd.), and HYA was prepared according to the method described in patent document 2 and used. Other starting compounds and reagents were commercially available products used as they were, or can be produced according to a method known per se, or a method analogous thereto.

[Example 1] Compound (1) of the Present Invention: ethyl 10-hydroxy-cis-12-octadecenoate In a 100 mL reaction vessel (medium bottle) were placed HYA (5 g), transesterification enzyme (lipase) (Novozymes A/S, Lipozyme RMIM, 1 g), and ethanol (5 g), the gaseous phase of the reaction system was replaced with nitrogen gas, and the mixture was stirred at 40° C. for 28 hr. The transesterification enzyme was removed by filtration through a filter paper and the filtrate was concentrated to give ethyl 10-hydroxy-cis-12-octadecenoate (5.5 g; yield 100%).

Melting point: not more than −20° C.;
$^1$H NMR (CDCl$_3$, 500 MHz): (δ) ppm: 0.89 (t, 3H, J=6.9 Hz), 1.30 (m, 19H), 1.46 (m, 2H), 1.61 (tt, 2H, J=7.3, 7.3 Hz), 2.05 (dt, 2H, J=7.0, 7.3 Hz), 2.21 (dd, 2H, J=6.8, 6.8 Hz), 2.28 (t, 2H, J=7.6 Hz), 3.61 (tt, H, J=5.9, 6.0 Hz), 4.12 (q, 2H, J=7.2 Hz), 5.40 (dt, 1H, J=7.5, 11.0 Hz), 5.57 (dt, 1H, J=7.4, 10.9 Hz); MS(ESI): M$^+$ 326.

[Example 2] Compound (1) of the Present Invention: propyl 10-hydroxy-cis-12-octadecenoate In a 100 mL reaction vessel (medium bottle) were placed HYA (0.5 g), transesterification enzyme (lipase) (Novozymes A/S, Lipozyme RMIM, 0.1 g), and propanol (0.5 g), the gaseous phase of the reaction system was replaced with nitrogen gas, and the mixture was stirred at 40° C. for 14.5 hr. The transesterification enzyme was removed by filtration through a filter paper and the filtrate was concentrated to give propyl 10-hydroxy-cis-12-octadecenoate (0.5 g; yield 88%).

Melting point: not more than −20° C.;
$^1$H NMR (CDCl$_3$, 500 MHz): (δ) ppm: 0.89 (t, 3H, J=6.9 Hz), 0.95 (t, 3H, J=7.4 Hz), 1.30 (m, 16H), 1.47 (m, 2H), 1.64 (m, 4H), 2.05 (dt, 2H, J=5.7, 7.6 Hz), 2.21 (dd, 2H, J=6.6, 6.6 Hz), 2.30 (t, 2H, J=7.6 Hz), 3.61 (tt, 1H, J=5.9, 6.0 Hz), 4.02 (t, 2H, J=6.7 Hz), 5.40 (dt, 1H, J=6.8, 10.9 Hz), 5.57 (dt, 1H, J=7.3, 10.9 Hz);
MS(ESI): M$^+$ 340.

[Example 3] Compound (2) of the Present Invention: monoester of 10-hydroxy-cis-12-octadecenoic acid with ethylene glycol, and Compound (3) of the Present Invention: diester of 10-hydroxy-cis-12-octadecenoic acid with ethylene glycol In a 100 mL reaction vessel (medium bottle) were placed HYA (0.5 g), transesterification enzyme (lipase) (Novozymes A/S, Lipozyme RMIM, 0.1 g), and ethylene glycol (260.7 mg), the gaseous phase of the reaction system was replaced with nitrogen gas, and the mixture was stirred at 40° C. for 72 hr. The transesterification enzyme was removed by filtration through a filter paper and the filtrate was isolated and purified by moderate-pressure silica gel chromatography ("Flash automatic purification apparatus Isolera One", manufactured by Biotage AB, column: "SNAP Ultra", manufactured by Biotage AB, eluted with hexane: ethyl acetate=90:10-50:50) to give monoester of 10-hydroxy-cis-12-octadecenoic acid with ethylene glycol (315.6 mg) and diester of 10-hydroxy-cis-12-octadecenoic acid with ethylene glycol (152.7 mg).

Monoester of 10-hydroxy-cis-12-octadecenoic acid with ethylene glycol

Melting point: not more than 8-9° C.;
$^1$H NMR (CDCl$_3$, 500 MHz): (δ) ppm: 0.89 (t, 3H, J=7.0 Hz), 1.30 (m, 16H), 1.46 (m, 2H), 1.63 (tt, 2H, J=7.3, 7.3 Hz), 1.84 (brs, 1H), 2.05 (dt, 2H, J=5.2, 6.5 Hz), 2.21 (dd, 2H, J=6.5, 6.5 Hz), 2.35 (t, 2H, J=7.5 Hz), 3.48 (brs, 1H), 3.61 (tt, 1H, J=5.8, 6.2 Hz), 4.21 (t, 2H, J=1.7 Hz), 5.40 (dt, 1H, J=7.5, 11.0 Hz), 5.57 (dt, 1H, J=7.4, 10.9 Hz);
MS(ESI): M$^+$ 342.

Diester of 10-hydroxy-cis-12-octadecenoic acid with ethylene glycol

Melting point: 22° C.;
$^1$H NMR (CDCl$_3$, 500 MHz): (δ) ppm: 0.89 (t, 6H, J=7.0 Hz), 1.30 (m, 32H), 1.46 (m, 4H), 1.62 (tt, 4H, J=7.1, 9.1 Hz), 2.05 (dt, 4H, J=6.1, 7.4 Hz), 2.21 (dd, 4H, J=6.7, 6.7 Hz), 2.32 (m, 4H), 3.48 (brs, 2H), 3.61 (tt, 2H, J=5.8, 6.3 Hz), 4.27 (brs, 4H), 5.40 (dt, 2H, J=7.5, 11.0 Hz), 5.57 (dt, 2H, J=7.3, 11.0 Hz);
MS(ESI): M$^+$ 623.

[Comparative Example]
10-Hydroxy-cis-12-octadecenoic acid (HYA)

As Comparative Example, HYA prepared according to the method described in patent document 2 was used.

Experimental Example 1

Whether the compounds of Examples 1 and 2 and HYA of Comparative Example are liquid or solid at ambient temperature (about 15-25° C.) was confirmed by visual observation.

As a result, the compounds of Examples 1 and 2 were liquid at ambient temperature, and HYA of Comparative Example was solid at ambient temperature.

Therefore, it was found that the compound of the present invention in which 10-hydroxy-cis-12-octadecenoic acid (HYA) is converted to ethyl ester or propyl ester thereof exists in a liquid state at ambient temperature.

Experimental Example 2

A sensory evaluation of the flavor of compound of Example 1, and HYA of Comparative Example was performed by 10 panelists (hereinafter to be referred to as taste test). The panelists ingested 5 mg of a sample (sample name was kept secret to the panelists during the test), evaluated five tastes (umami taste, bitter taste, sour taste, saltiness, sweetness) respectively for the acridity and oil odor, and made total evaluation.

Each evaluation was marked in the following 5 grades and an average score of the 10 panelists was calculated.

Five tastes (umami taste, bitter taste, sour taste, saltiness, sweetness):

Strong (5 points) - weak (1 point)
Acridity: weak (5 points) - strong (1 point)
Oil odor: weak (5 points) - strong (1 point)
Total evaluation: delicious (5 points) - brackish (1 point)

As a result, as shown in Table 1 below, HYA of Comparative Example showed strong acridity and a moderate oil odor, whereas the compound of Example 1 of the present invention obtained high evaluation of umami taste and sweetness as compared to Comparative Example, and showed remarkably reduced acridity and a somewhat reduced oil odor. Furthermore, the total evaluation was also high.

TABLE 1

|  | State at standard temperature | Results of taste test | | | | | | | |
|---|---|---|---|---|---|---|---|---|---|
|  |  | Five tastes | | | | | | | |
|  |  | umami taste | bitter taste | sour taste | saltiness | sweetness | acridity | oil odor | total evaluation |
| Ex. | liquid | 3.0 | 2.5 | 1.5 | 2.0 | 3.0 | 3.0 | 3.5 | 3.5 |
| Comp. Ex. | solid | 1.5 | 3.5 | 1.5 | 1.5 | 1.0 | 1.0 | 3.0 | 1.5 |

From the above results, it was found that the compound of the present invention can be present as liquid at ambient temperature by lowering the melting point. In addition, the compound of Example 1 could be confirmed to have no acridity and shows a strong umami taste.

INDUSTRIAL APPLICABILITY

It was found that compound of the present invention is liquid at ambient temperature and has a good flavor, and permits easy ingestion and easy handling. In addition, in the compound of the present invention, the ester bond is hydrolyzed by lipase or the like in the body after ingestion to liberate HYA. Thus, superior physiological functions (lipid metabolic abnormality improving effect, action to increase intestinal immunity, intestinal inflammation suppressive action, etc.) as well as when HYA itself is ingested singly are expected to be exerted. Therefore, the compound is industrially extremely useful in that it can be utilized as edible fat or oil utilizing the above-mentioned functions and can also be utilized as every kind of food or food additive and further, utilized in various fields such as pharmaceutical product, cosmetic, feed and the like.

This application is based on a patent application No. 2015-112606 filed in Japan, the contents of which are incorporated in full herein.

The invention claimed is:

1. A $C_{1-40}$ alkyl ester of 10-hydroxy-cis-12-octadecenoic acid or an optical isomer thereof, excluding methyl 10-hydroxy-cis-12-octadecenoate and ethyl 10-hydroxy-cis-12-octadecenoate.

2. The $C_{1-40}$ alkyl ester of 10-hydroxy-cis-12-octadecenoic acid or an optical isomer thereof according to claim 1, which is liquid at ambient temperature.

3. Edible fat or oil comprising a $C_{1-40}$ alkyl ester of 10-hydroxy-cis-12-octadecenoic acid or an optical isomer thereof, excluding methyl 10-hydroxy-cis-12-octadecenoate.

4. A food or food additive comprising a $C_{1-40}$ alkyl ester of 10-hydroxy-cis-12-octadecenoic acid or an optical isomer thereof, excluding methyl 10-hydroxy-cis-12-octadecenoate and at least one substance selected from the group consisting of nutrients, vitamins, minerals, dietary fiber, food with reported physiological function, and general food additives.

5. A pharmaceutical composition comprising a $C_{1-40}$ alkyl ester of 10-hydroxy-cis-12-octadecenoic acid or an optical isomer thereof, excluding methyl 10-hydroxy-cis-12-octadecenoate and one or more pharmaceutically acceptable additives.

6. A cosmetic or cosmetics additive comprising a $C_{1-40}$ alkyl ester of 10-hydroxy-cis-12-octadecenoic acid or an optical isomer thereof, excluding methyl 10-hydroxy-cis-12-octadecenoate and one or more additives which are generally used for cosmetics.

7. A feed or feed additive comprising a $C_{1-40}$ alkyl ester of 10-hydroxy-cis-12-octadecenoic acid or an optical isomer thereof, excluding methyl 10-hydroxy-cis-12-octadecenoate and one or more filler substances, dilution substances, and combinations thereof for feed.

8. An ester of 10-hydroxy-cis-12-octadecenoic acid with $C_{1-8}$ alkyleneglycol, or an optical isomer thereof.

9. The ester or an optical isomer thereof according to claim 8, which is liquid at ambient temperature.

10. A food or food additive comprising the ester or an optical isomer thereof according to claim 8.

11. A pharmaceutical composition comprising the ester or an optical isomer thereof according to claim 8 and one or more pharmaceutically acceptable additives.

12. A cosmetic or cosmetics additive comprising the ester or an optical isomer thereof according to claim 8 and one or more additives which are generally used for cosmetics.

13. A method of treating a disease comprising administering an effective amount of the pharmaceutical composition of claim 5 to an animal having a disease selected from the group consisting of obesity, diabetes, hyperlipidemia, fatty liver, ulcerative colitis, Crohn's disease, ulcer, and irritable bowel syndrome, thereby treating the disease in the animal.

14. The $C_{1-40}$ alkyl ester of claim 1, wherein the $C_{1-40}$ alkyl ester is a $C_{1-6}$ alkyl ester of 10-hydroxy-cis-12-octadecenoic acid or an optical isomer thereof, excluding methyl 10-hydroxy-cis-12-octadecenoate and ethyl 10-hydroxy-cis-12-octadecenoate.

15. The edible fat or oil of claim 3, comprising a $C_{1-6}$ alkyl ester of 10-hydroxy-cis-12-octadecenoic acid or an optical isomer thereof, excluding methyl 10-hydroxy-cis-12-octadecenoate.

16. An ester of 10-hydroxy-cis-12-octadecenoic acid with $C_{2-6}$ alkyleneglycol, or an optical isomer thereof.

* * * * *